United States Patent
Totani et al.

(10) Patent No.: US 6,332,355 B1
(45) Date of Patent: Dec. 25, 2001

(54) METHOD OF ESTIMATING A LIFE OF BALL SCREW INCLUDED IN ELECTRIC INJECTION MOLDING MACHINE AND LIFE ESTIMATING SYSTEM

(75) Inventors: Tsuginobu Totani, Numazu; Kiyoshi Sasaki, Mishima; Akira Kanda, Numazu; Yukio Iimura; Jun Koike, both of Shimizu-Cho; Fumiyuki Katoh, Nagaizumi-Cho; Masahiro Tamaki, Susono; Yutaka Yamaguchi, Kannami-Cho, all of (JP)

(73) Assignee: Toshiba Kikai Kabushiki Kaisha, Tokyo-to (JP)

( * ) Notice: Subject to any disclaimer, the term of this patent is extended or adjusted under 35 U.S.C. 154(b) by 0 days.

(21) Appl. No.: 09/506,681

(22) Filed: Feb. 18, 2000

(30) Foreign Application Priority Data

Feb. 19, 1999 (JP) ................................. 11-042123

(51) Int. Cl.$^7$ ..................................................... G01M 5/00
(52) U.S. Cl. ............................................................. 73/162
(58) Field of Search .............................. 73/865.9, 862.53, 73/862.542, 862.27, 162; 74/DIG. 7

(56) References Cited

U.S. PATENT DOCUMENTS

| | | | |
|---|---|---|---|
| 4,733,361 | * | 3/1988 | Krieser et al. . |
| 5,749,265 | * | 5/1998 | Namimatsu et al. . |
| 6,082,209 | * | 7/2000 | Yabe et al. . |

\* cited by examiner

*Primary Examiner*—Robert Raevis
(74) *Attorney, Agent, or Firm*—Pillsbury Winthrop LLP

(57) ABSTRACT

An injection unit including a heating barrel and an injection screw rotationally and axially movable and placed in the heating barrel is disposed on one side of a clamping mechanism for clamping a mold. The injection screw is driven and controlled for operation through a ball screw by an electric motor. Products, each of a moving speed of the ball screw and an operating current supplied to the electric motor in a unit time, are accumulated to calculate a total energy value indicating the amount of total energy supplied to the ball screw. A life energy value is predetermined on the basis of products, each of force generated by the ball screw and a moving speed of the ball screw. It is decided that a life of the ball screw has terminated when the total energy value A is equal to or greater than the life energy B (A≧B).

7 Claims, 2 Drawing Sheets

METHOD OF ESTIMATING A LIFE OF BALL SCREW INCLUDED IN ELECTRIC INJECTION MOLDING MACHINE AND LIFE ESTIMATING SYSTEM

BACKGROUND OF THE INVENTION

1. Field of the Invention

The present invention relates to a method of estimating a life of a ball screw for moving an injection screw included in an electric injection molding machine and generating an alarm or the like, and a life estimating system for carrying out the method.

2. Description of the Related Art

In an electric injection machine, an injection screw is reciprocated axially by rotating a ball screw by an electric motor. Therefore, the greatest load is exerted on the ball screw during an injection molding operation. If the ball screw is damaged during a long period of use, it is expected that the operation of the injection molding machine must instantly be stopped. If such a situation takes place, the broken ball screw must immediately be replaced with a new one, which interrupts the operation of the associated production line, adversely affecting the stability of the quality of moldings and may possibly cause damage in component parts associated with the ball screw.

To avid such a situation it is desired to estimate time when the condition of the ball screw is close to a condition that causes damage to the ball screw, i.e., to estimate the life of the ball screw, and to replace the ball screw with a new one before the same is broken.

Generally, it has been a general practice to decide the life of the ball screw by the intuition of an operator skilled in the operation of the injection molding machine and to change the ball screw when the operator decided that the life of the ball screw has almost terminated. It is difficult to estimate the life of the ball screw accurately only by the operator's intuition. The usable ball screw is thrown away and time and labor is wasted for the unnecessary change of the usable ball screw if the usable ball screw is changed too early. The ball screw will be broken and serious damage will be made to the associated component parts if the time for changing the ball screw is delayed excessively.

From such a point of view, a life estimating apparatus for estimating the life of a rotary member included in an injection molding machine or the like proposed in JP-A No. Hei 6-91683 is capable of accurately estimating, on the basis of a recognition that bearings supporting the ball screw is a most heavily loaded member, the life of a rotary member, such as a bearing or a ball screw.

This previously proposed life estimating apparatus comprises a revolution counter for directly or indirectly counting the number of revolutions of a rotary member driven for rotation by a driving motor, an arithmetic unit capable of calculating a fatigue life of the rotary member on the basis of the number of revolutions of the rotary member and torque required to rotate the rotary member, and a comparator for comparing the total number of revolutions of the rotary member counted by the revolution counter and fatigue life of the rotary member calculated by the arithmetic unit, and provides a warning when the total number of revolutions of the rotary member approaches or arrives at the fatigue life to prompt the operator to replace the rotary member with a new one.

The foregoing prior art life estimating apparatus for estimating the life of a rotary member included in an injection molding machine or the like compares a numerical value indicating the counted total number of revolutions of the rotary member, and a numerical value representing the fatigue life calculated on the basis of the torque of the driving motor required to drive the rotary member for rotation, and uses a condition where the difference between those numerical values is practically naught as a criterion for deciding the life of the rotary member. Particularly, an arithmetic procedure for calculating the fatigue life on the basis of the torque is very complicated and, if the life of the bearing is used for life estimation, many parameters in addition to the torque of the driving motor are necessary and the arithmetic procedure becomes further complicated.

SUMMARY OF THE INVENTION

Accordingly, it is an object of the present invention to provide a method of estimating a life of a ball screw included in an electric injection molding machine, capable of appropriately and surely estimating the life of a ball screw by a simple arithmetic procedure, and to provide a life estimating apparatus capable of estimating the life of a ball screw by a simple arithmetic procedure, having a simple configuration and capable of being manufactured at a low cost.

The present invention provide, a method of estimating a life of a ball screw included in an electric injection molding machine comprising an injection unit having a heating barrel and an injection screw placed for rotation in the heating barrel, and an electric motor connected to the injection screw by the ball screw; said method comprising the steps of determining a total energy value indicating an amount of total energy supplied to the ball screw on the basis of operating conditions of the ball screw and the electric motor and deciding whether or not the life of a ball screw has terminated by comparing a predetermined life energy value for the ball screw determined on the basis of force generated by the ball screw and moving speed of the ball screw, and the total energy value.

The present invention provides a life estimating apparatus for estimating a life of a ball screw included in an electric injection molding machine comprising an injection unit having a heating barrel and an injection screw placed for rotation in the heating barrel, and an electric motor connected to the injection unit by the ball screw, said life estimating apparatus comprising an encoder connected to the electric motor an arithmetic-and-storage means for multiplying a moving speed of the ball screw in a unit time measured by the encoder, and an operating current supplied to the electric motor together during this time, and accumulating products, each formed by multiplying the moving speed of the ball screw and the operating current supplied to the electric motor in the unit time, and storing the accumulated products as cumulative data and a life deciding means for determining a total energy value indicating an amount of total energy supplied to the ball screw on the basis of the cumulative data stored in the arithmetic-and-storage means, and comparing the total energy value, and a predetermined life energy value for the ball screw determined on the basis of force generated by the ball screw and the moving speed of the ball screw to decide whether or not the life of a ball screw has terminated.

The present invention provides a life estimating apparatus for estimating a life of a ball screw included in an electric injection molding machine comprising an injection unit having a heating barrel and an injection screw placed for rotation in the heating barrel, and an electric motor connected to the injection screw by the ball screw, said life estimating apparatus comprising an encoder connected to the electric motor a torque meter interposed between the ball screw and the electric motor an arithmetic-and-storage means for multiplying a moving speed of the ball screw in a unit time measured by the encoder and a torque of the ball screw during this time measured by the torque meter together, and accumulating products, each formed by multiplying the moving speed of the ball screw and the torque of the ball screw in the unit time, and storing the accumulated products as cumulative data and a life deciding means for determining a total energy value indicating an amount of total energy supplied to the ball screw on the basis of the cumulative data stored in the arithmetic-and-storage means, and comparing the total energy value, and a predetermined life energy value for the ball screw determined on the basis of force generated by the ball screw and the moving speed of the ball screw to decide whether or not the life of a ball screw has terminated.

DESCRIPTION OF THE PREFERRED EMBODIMENTS

Basic Principle

The inventors of the present invention made studies and examinations earnestly and found that it is possible to decide that a life of a ball screw has terminated when a total energy amount A, i.e., the amount of total energy supplied to the ball screw, determined by accumulating the products, each of a moving speed v of the ball screw in a unit time and an operating current I supplied to an electric motor for driving the ball screw for rotation during this time has increased beyond a predetermined life energy value B included in a table of life energy values determined beforehand on the basis of the product of force F exerted by the ball screw and the moving speed v taking into consideration the relation of life dependent on force exerted on the ball screw and time ($A \geq B$).

The inventors of the present invention also found, through studies, that torque necessary for rotating the ball screw measured by a torque meter disposed at the joint of the drive shaft of the electric motor and the ball screw is proportional to driving current supplied to the electric motor, a total energy value A', i.e., the amount of total energy supplied to the ball screw, can be determined by accumulating the products each, of moving speed v of the ball screw in the unit time and torque during this time, and the life of a ball screw can be decided by comparing the total energy amount A' and the life energy value B.

It was found also that it is possible to decide the life of a ball screw, when the torque is measured, by measuring delay time between time when the electric motor is actuated and time when torque necessary for rotating the ball screw increases to a predetermined torque. It was also found that it is possible to decide the life of the ball screw, when a load is driven through the ball screw by the electric motor, on the basis of the width of the range of variation of measured torques varying in a predetermined torque range.

Preferred Embodiments

A method of estimating the life of a ball screw included in an electric injection molding machine in accordance with the present invention and a life measuring apparatus for carrying out the method will be describe hereinafter with reference to the accompanying drawings.

First Embodiment

Figure 1:
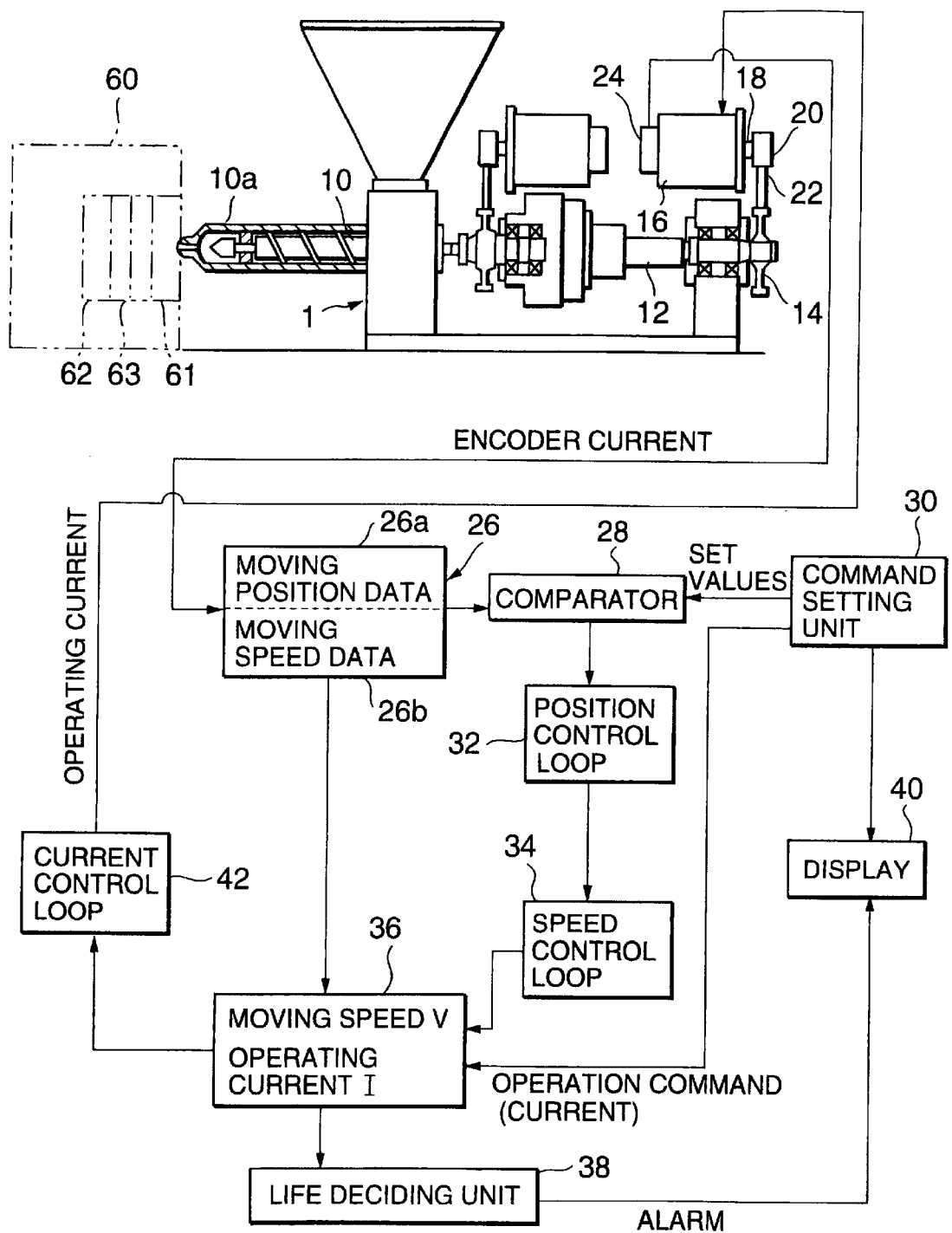
FIG. 1 is a schematic front elevation of an essential portion of a life estimating apparatus in a preferred embodiment according to the present invention for carrying out a life estimating method in accordance with the present invention for estimating a life of a ball screw included in an electric injection molding machine, and a block diagram of a control system, respectively.

FIG. 1 is a schematic front elevation of an essential portion of a life estimating apparatus in a first embodiment according to the present invention for carrying out a life estimating method in accordance with the present invention for estimating the life of a ball screw included in an electric injection molding machine, and a block diagram of a control system, respectively.

Referring to FIG. 1, the electric injection molding machine has an injection unit 1 having a heating barrel 10$a$ and an injection screw 10 placed for rotation in the heating barrel 10$a$, and an electric motor 16 operatively connected to the injection screw 10 by a ball screw 12 and a pulley 14.

The injection screw 10 is connected to the ball screw so as to be rotatably movable by the ball screw rotating. The pulley 14 is attached to one end of the ball screw 12. The electric motor 16 is disposed with its axis extended in parallel to the axis of the ball screw 12. A pulley 20 is attached to the output shaft 18 of the electric motor 16. A timing pulley belt 22 is wound around the pulley 20 and the pulley attached to one end of the ball screw 12.

The electric injection molding machine has a mold 63 disposed in front of the forward end of the injection screw 10, and a mold clamping mechanism 60 including a stationary mold platen 61 disposed on one side of the mold 63 and a movable mold platen 62 disposed on the other side of the mold 63 to open and close the mold 63.

The injection unit 1 is operated by driving the ball screw by the electric motor 16. The ball screw is the object of operation of the life estimating method and the life estimating apparatus of the present invention.

An encoder 24 capable of measuring position and speed is combined with the electric motor 16 to measure the position and the moving speed of the ball screw 12 when the electric motor 16 drives the ball screw 12. A measuring unit 26 is connected to the encoder 24. Position data 26$a$ and moving speed data 26$b$ are produced by the encoder 24 and the measuring unit 26, and a moving speed v is calculated on the basis of the moving speed data 26$b$. The moving speed V is given to an arithmetic-and-storage unit 36. The arithmetic-and-storage unit 36 accumulates products each of moving speed v and an operating current I specified by the command setting unit 30 and stores the products as cumulative data. The moving speed v can be determined also from the difference between signals provided by a comparator 28, position control loop 32 and a speed control loop 34 for the feedback control of the electric motor 16, which will be described later, and the command setting unit 30.

The cumulative data held by the arithmetic-and-storage unit 36 is obtained by accumulating the products of the moving speed v and the operating current I in a unit operating time and is expressed by:

$$I_1 \times v_1 + I_2 \times v_2 + \ldots = \Sigma(I_n \cdot v_n)$$

A life deciding unit 38 multiplies the cumulative data held by the arithmetic-and-storage unit 36 by a torque constant k for the electric motor 16 to calculate a total energy amount A, i.e., the amount of total energy supplied to the ball screw 12.

The life deciding unit 38 has a table showing a life formulated on the basis of the relationship between a force applied to the ball screw 12 and a time for which the force is applied to the ball screw 12. That is, the table contains predetermined life energy values B represented by the products of force F applied to the ball screw 12 and moving speed v of the ball screw 12. The life deciding unit 38 compares the total energy amount A with a desirable life energy value B and decides that the life of the ball screw has terminated when the total energy value A is equal to or greater than the life energy value B (A≧B).

If the life deciding unit 38 decides that the life of the ball screw 12 has terminated, the life deciding unit 38 can generate a necessary alarm and a display 40 can displays this situation.

The set values specifying the operations are sent to a comparator 28 of the electric motor 16 set by the command setting unit 30 can be displayed on the display 40. The set values specifying the operations and results of comparison made by the comparator 28 are sent through the position control loop 32, the speed control loop 34 and the arithmetic-and-storage unit 36 to a current control loop 42 for the feedback control of the electric motor 16.

Second Embodiment

Figure 2:
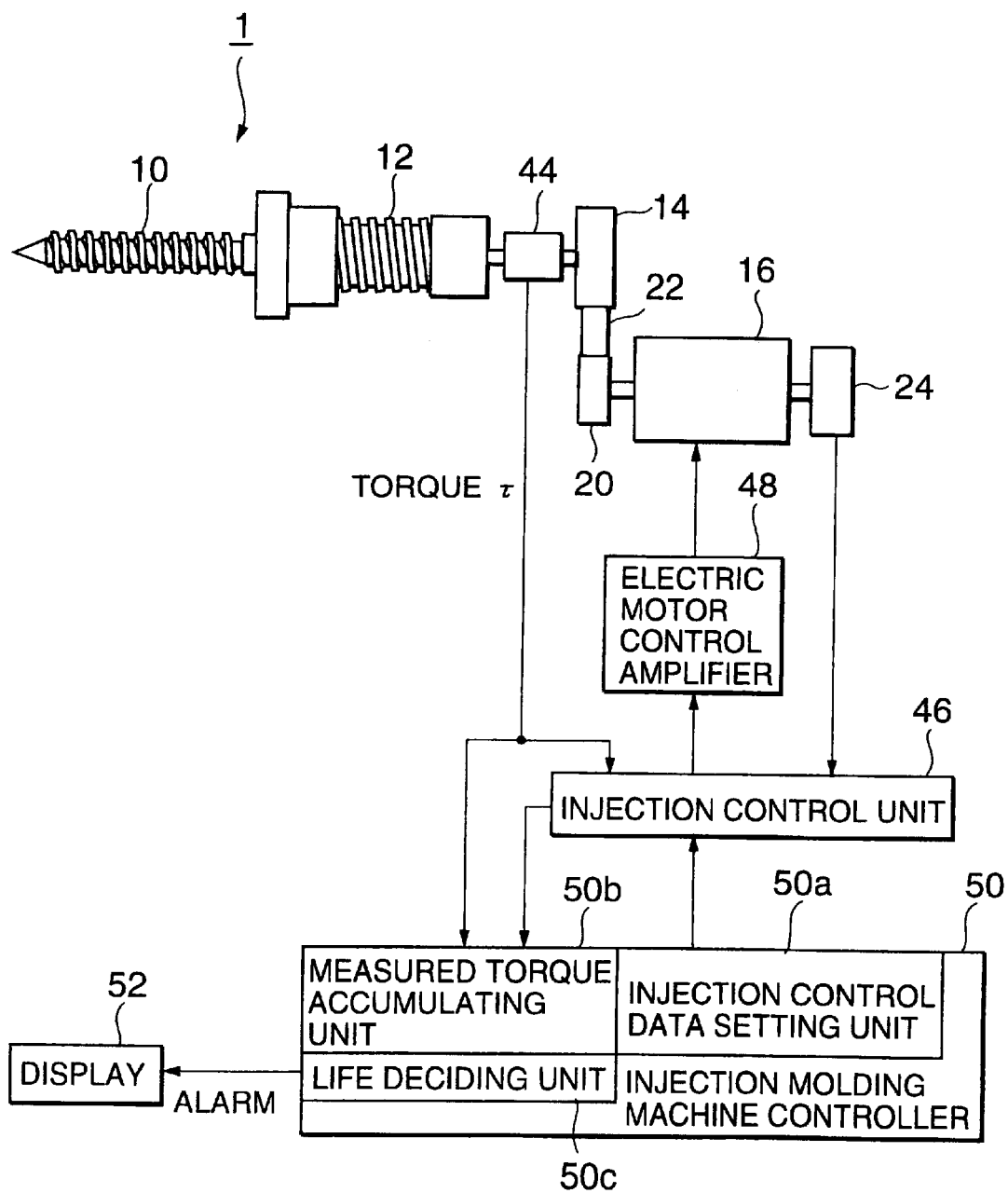
FIG. 2 is a block diagram of an essential portion of a life estimating apparatus in another embodiment according to the present invention for carrying out the life estimating method in accordance with the present invention for estimating the life of a ball screw included in an electric injection molding machine, and a control system.

FIG. 2 is a block diagram of an essential portion of a life estimating apparatus in another embodiment according to the present invention for carrying out the life estimating method in accordance with the present invention for estimating the life of a ball screw included in an electric injection molding machine, and a control system. In the following description, parts shown in FIG. 2 like or corresponding to those shown in FIG. 1 are denoted by the same reference characters and the description thereof will be omitted.

Referring to FIG. 2, a torque measuring device (torque meter) 44 is interposed between the drive shaft side of an electric motor 16 and a ball screw 12.

The torque measuring device 44 measures torque τ needed to rotate the ball screw 12. Torque τ to be measured is proportional to driving current I for driving the electric motor 16. Therefore, a total energy value A' can be determined by accumulating products, each of a moving speed of the ball screw 12 in a unit time measured by an encoder 24 and a torque τ during this time. The total energy value A' is compared with a life energy value B predetermined by a method as mentioned in the description of the first embodiment to decide the life of the ball screw 12.

In the second embodiment, the torque τ measured by the torque measuring device 44, and position data and moving speed data representing a position and a moving speed of the ball screw are provided by an encoder 24 (FIG. 1) are combined with the electric motor 16, and are given to an injection control unit 46. The injection control unit 46 controls the electric motor 16 on the basis of operation commands set in an injection control data setting unit 50a of an injection molding machine controller 50.

The injection control unit 46 is capable of controlling the electric motor 16 through an electric motor control amplifier 48 on the basis of the measured torque τ, the position data and the moving speed data in a feedback control mode.

The torque τ measured by the torque measuring device 44 is multiplied by the moving speed v, and is given to a measured torque accumulating unit (arithmetic-and-storage means) 50b included in the injection molding machine controller 50. The measured torques τ are accumulated successively. The accumulated measured torques τ, similarly to those in the first embodiment, are multiplied by the moving speed v of the ball screw 12, and the measured torque accumulating unit 50b accumulates the products each of the torque τ and the moving speed V of the ball screw 12.

A life deciding unit 50c included in the injection molding machine controller 50 calculates a total energy value A' on the basis of the cumulative data accumulated in the measured torque accumulating unit 50b. At the same time, the life deciding unit 50c compares the total energy value A' with a life energy value B obtained by a method similar to that employed in the first embodiment, and decides that the life of the ball screw 12 has terminated when the total energy value A' is equal to or greater than the life energy value B (A'≧B).

If the life deciding unit 50c decides that the life of the ball screw 12 has terminated, the life deciding unit 50c can generated a necessary alarm and a display 52 can display this situation.

When a load is driven through the ball screw 12 by the electric motor 16, the life deciding unit 50c may estimate the life of the ball screw 12 on the basis of the width of the range of variation of measured torques varying in a predetermined torque range.

Although the invention has been described in its preferred embodiments, the present invention is not limited thereto in its practical application and many changes may be made in design data without departing from the scope and spirit of the present invention.

As apparent from the description of the first and the second embodiment, according to the present invention, the method of estimating the life of the ball screw of the electric injection molding machine having the injection unit 1 that drives the injection screw 10 placed for rotation and axial movement in the heating barrel 10a disposed on one side of the mold clamping mechanism 60 to inject a molten resin into the mold 63, can calculate the total energy value A representing the amount of total energy supplied to the ball screw by multiplying the product of the moving speed of the ball screw in the unit time and the driving current supplied to the electric motor by the torque constant for the electric motor during this time, and can set the life energy value B on the basis of the product of the force applied to the ball screw and the moving speed of the ball screw, and can decide that the life of the ball screw has terminated when the total energy value A is equal to or greater than the life energy value B(A≧B). Thus the method is capable of properly and simply deciding the termination of the life of the ball screw.

The life estimating apparatus for carrying out the method has the encoder combined with the electric motor to measure the position and the moving speed of the ball screw, and the arithmetic-and-storage unit multiplies the moving speed in the unit time of the ball screw and the operating current for the electric motor together during this time and accumulates the product. The life deciding unit calculates the total energy amount A representing the amount of total energy supplied to the ball screw and decides the life of the ball screw by comparing the total energy value A with the predetermined life energy value B. The results of a decision made by the life deciding unit is displayed by a display. The life estimating apparatus has a simple configuration and can be manufactured at a low cost.

What is claimed is:

1. A method of estimating a life of a ball screw included in an electric injection molding machine comprising an injection unit having a heating barrel and an injection screw placed for rotation in the heating barrel, and an electric motor connected to the injection screw by a ball screw; said method comprising the steps of:

determining a total energy value indicating an amount of total energy supplied to the ball screw on the basis of operating conditions of the ball screw on the basis of operating conditions of the ball screw and the electric motor; and deciding whether or not the life of the ball screw has terminated by comparing a predetermined life energy value for the ball screw that is associated with force generated by the ball screw and moving speed of the ball screw, and the total energy value.

2. The method of estimating a life of a ball screw included in an electric injection molding machine according to claim 1, wherein the total energy value indicating an amount of total energy supplied to the ball screw is determined by accumulating products, each of a moving speed of the ball screw in a unit time and an operating current supplied to the electric motor during this time.

3. The method of estimating a life of a ball screw included in an electric injection molding machine according to claim 1, wherein the total energy value indicating an amount of total energy supplied to the ball screw is determined by accumulating products each of a moving speed of the ball screw in a unit time and a torque applied to the ball screw during this time.

4. A life estimating apparatus for estimating a life of a ball screw included in an electric injection molding machine comprising an injection unit having a heating barrel and an injection screw placed for rotation in the heating barrel, and an electric motor connected to the injection screw by a ball screw, said life estimating apparatus comprising:

an encoder connected to the electric motor;

an arithmetic-and-storage means for multiplying a moving speed of the ball in a unit time measured by the encoder, and an operating current supplied to the electric motor together during this time, and accumulating products, each formed by multiplying the moving speed of the ball screw and the operating current supplied to the electric motor in the unit time, and storing the accumulated products as cumulative data; and a life deciding means for determining a total energy amount indicating an amount of total energy supplied to the ball screw on the basis of the cumulative data stored in the arithmetic-and-storage means, and comparing the total energy value, and a predetermined life energy value for the ball screw that is associated with force generated by the ball screw and the moving speed of the ball screw to decide whether or not the life of a ball screw has terminated.

5. The life estimating apparatus for estimating a life of a ball screw included in an electric injection molding machine according to claim 4, wherein a display means for displaying a result made by a life deciding means is connected to the life deciding means.

6. A life estimating apparatus for estimating a life of a ball screw included in an electric injection molding machine comprising an injection unit having a heating barrel and an injection screw placed for rotation in the heating barrel, and an electric motor connected to the injection screw by a ball screw, said life estimating apparatus comprising:

an encoder connected to the electric motor;

a torque meter interposed between the ball screw and the electric motor;

an arithmetic-and-storage means for multiplying a moving speed of the ball in a unit time measured by the encoder, and an operating current supplied to the electric motor together during this time measured by the torque meter together, and accumulating products, each formed by multiplying the moving speed of the ball screw and the torque of the ball screw in the in the unit time, and storing the accumulated products as cumulative data; and a life deciding means for determining a total energy value indicating an amount of total energy supplied to the ball screw on the basis of the cumulative data stored in the arithmetic-and-storage means, and comparing the total energy value, and a predetermined life energy value for the ball screw that is associated with force generated by the ball screw and the moving speed of the ball screw to decide whether or not the life of a ball screw has terminated.

7. The life estimating apparatus for estimating a life of a ball screw included in an electric injection molding machine according to claim 6, wherein a display means for displaying a result made by the life deciding means is connected to the life deciding means.

* * * * *